United States Patent [19]

Kaufman et al.

[11] Patent Number: 4,596,723

[45] Date of Patent: Jun. 24, 1986

[54] IMMUNOASSAY SUBSTRATE

[75] Inventors: Nancy K. Kaufman, Belmont; Richard A. Harte, Redwood City; Anthony B. Chen, Hayward, all of Calif.

[73] Assignee: Daryl Laboratories, Inc., Santa Clara, Calif.

[21] Appl. No.: 606,387

[22] Filed: May 2, 1984

[51] Int. Cl.$^4$ .................. B05D 3/02; G01N 33/54
[52] U.S. Cl. .................. 427/336; 427/374.1; 427/379; 427/398.1; 428/327; 435/7; 436/518; 436/528; 436/531; 436/535
[58] Field of Search .................. 427/336, 374.1, 379, 427/398.1; 435/7; 436/518, 528, 531, 535; 428/327

[56] References Cited

U.S. PATENT DOCUMENTS 4,340,564 7/1982 Harte et al. .................. 435/7 X
4,540,660 9/1985 Harte et al. .................. 436/518 X

*Primary Examiner*—Michael R. Lusignan
*Attorney, Agent, or Firm*—Kolisch, Hartwell & Dickinson

[57] ABSTRACT

Preparation of an immunoassay gel substrate which includes the steps of depositing on an immobilizing support structure a liquid mass of a gel-forming emulsion which coalesces into a thick gel-like matrix film characterized by substantial non-agglomerated matrix homogeneity, treating the resulting film to alter matrix homogeneity by agglomerating particles which form part of the gel, and as a consequence of the treating step establishing the object gel. Treating may be performed either by subjecting the gel to multiple time-vigorous water-wash and dry cycles, by emersing the gel in water for a relatively long period of time, or by wetting the gel and then subjecting it to one or more freeze/thaw cycles.

15 Claims, No Drawings

IMMUNOASSAY SUBSTRATE

BACKGROUND AD SUMMARY OF TE INVENTION

This invention pertains to an improved three-dimensionally-extensive, water-swellable, matrix-like, protein-binding gel for use in solid phase immunoassay testing, and in particular, to a significant novel method of preparing such a gel.

The subject matter of the instant invention relates, more specifically, to an improvement in the method for making a gel having a material composition initially formed as described in the now co-pending, prior-filed patent application of Richard A. Harte, Anthony B. Chen and Nancy K. Kaufman, Ser. No. 483,055, filed April 7, 1983, now U.S. Pat. No. 4,540,660, patented September 10, 1985, "SUBSTRATE FOR FLUOROIMMUNOASSAY OF BIOLOGICAL FLUIDS", the entire disclosure of which is incorporated herein by reference. Also incorporated by reference in the present application, for the purpose of providing useful background information, are the disclosures of co-pending, prior-filed U.S. patent applications of Anthony B. Chen, Richard A. Harte and Nancy K. Kaufman, Ser. No. 399,855, filed July 19, 1982, now U.S. Pat. No. Des. 279,817, patented July 23, 1985, "IMMUNOASSAY TEST SLIDE", and of Richard A. Harte and John F. Hencken, Ser. No. 362,696, filed March 29, 1982, for "MULTI-LABEL IMMUNOASSAY TESTING DEVICE".

Elaborating, by way of background, the field in which the present invention has utility and importance, solid phase immunoassay techniques have been employed for about the past two decades, offering the advantage that they represent an extremely easy way for the operator to separate bound reagents (bound to a solid substrate) from reacting biochemical agents which are still in the liquid phase (Catt, K. & Treager, G. W., Science, 158, p. 1570, 1967).

While prior art solid phase techniques tend to produce sensitive, relatively simple procedures, they are prone to a serious "background noise" problem in the form of "nonspecific binding". Such binding is generally the primary cause of problems like false positive reactions, distorted quantitation values, variability, and inability to determine clearly a positive/negative cut-off value—all leading to a large "grey" zone of ambiguity which adds expense and requires frustrating retesting of samples.

In a recent review of the state of the art in solid-phase nonisotopic assays (Boraker, D. K., "SOLID PHASE MATERIALS FOR NONISOTOPIC IMMUNOASSAYS", presented at Nonisotopic Immunoassays, a one-day comprehensive conference at the New York Hilton in New York, New York, July 25, 1983), the following statement appears:

There is clearly a tendency for proteins to bind to solid phase support materials in various ways which represent non-specific binding. Such binding often occurs even with our best efforts to stop it, (Detergents, blocking proteins, etc.) to the endless frustration of those who yearn for the opportunity to push these marvelous amplification systems of enzymes and chromogenic substrates to their theoretical limits.

The present invention, offering a significantly improved method of producing a gel structure like that described in above-referred-to patent application Ser. No. 483,055, relates to a recently developed matrix material for use in solid-phase type immunoassays. In this material, there exists a unique micro-structure that offers a significant advance for immunoassay applications—prime among them being the almost total lack of nonspecific binding, even in the presence of undiluted body fluids.

Further explaining the background of this invention, there are, basically, three methods of attachment for binding proteins to a solid material. Over the years, an extremely large number of materials have been employed for this purpose, and reported in the literature. For example, these materials have included metal films, films of plastic such as polystyrene, polyproplyene and various acrylics, silastics and rubber-like plastics, matted fiber beds of glass wool, nylon mesh, chemically treated cellulose mats, nitrocellulose, cellulose acetates and other mixed esters of cellulose, scintered materials like clay (bentonite, kaolin, etc.), charcoal particles, treated glass surfaces, natural fibers, and many others. The three methods employed with different types of these materials are adsorption, chemical (or covalent) linkage, and gel entrapment.

Adsorption, which is the simplest method of attachment, is the most widely employed one of the three today. This kind of attachment relies on weak, electrostatic Van der Waals forces, and hydrophobic or hydrophilic bonding. Hydrogen bonding, a somewhat stronger force, may also play some part in adsorption.

Typical of the prior art adsorption procedures is the binding of specific antibody proteins to the inner walls of a plastic (polystyrene) test tube, to "fish out" specific analyte from a mix of many biochemicals in blood serum or in other body fluids. Such was first described by Catt and Treager (cited earlier herein), and became the basis of many radioimmunoassay tests developed over the following years.

A similar adsorption technique, often applied to serologies (antibody detection), has been used more recently. This technique involves allowing specific antigen solutions to stand overnight in wells of a polystyrene or polypropylene microtiter plate, permitting slow adsorption of protein to the well bottom and walls. Thereafter, the antigen solution is poured off, and the well is filled with a noninvolved protein, like bovine serum albumin, whose purpose is to cover all of the remaining binding sites on the plastic which have not electrostatically bound the antigen protein. Obviously, all of the remaining unbound sites are a major source of nonspecific binding during an assay.

A further concern of adsorption-type binding, resulting from the presence of weak electrostatic or hydrophobic forces, is the ability to break bonds during the physically strenuous activity of washing which occurs during a typical assay. Of course, washing steps after incubation of reagents is essential to remove unbound reagents. The amount of specific protein lost as a consequence of washing during an assay may vary from test well to test well, and this is a major contributing factor to poor assay precision and lack of repeatability.

Chemical or covalent bonds are much more secure, and as a consequence, the loss of reagents during testing is significantly reduced. The problems associated with covalent-type binding, however, are not trivial. For example, very few natural surfaces present exposed covalent bonding sites to protein in solution. Accordingly, it is necessary that one activate a surface, chemically or by other means (such as by plasma activation, photoactivation, etc.). In the case of chemical activation, the chemicals employed (typically periodates, carbodiimides, etc.) are generally toxic, caustic, or hazardous in other ways. Also, it is difficult to prepare a batch of material which provides consistent degrees of surface activation. Nevertheless, the advantages of covalent binding are considered to be so significant that many people take the time and trouble to perform surface treatment using these hazardous activating reagents.

The third above-mentioned method of binding, gel entrapment, typically takes place in gels with either controlled or uncontrolled pore sizes associated therewith. For example, an illustrative prior-art gel material is described in U.S. Pat. No. 3,793,445, issued to Updike and Goodfriend on February 19, 1974 for "REAGENT FOR RADIOIMMUNOASSAY", and U.S. Pat. No. 3,970,429, issued to Updike on July 20, 1976 for "METHOD FOR IMMUNOLOGIC DETERMINATION".

A general object of the present invention is to provide a method for achieving a unique gel structure which, in many ways, combines the most desirable properties of both prior art gel entrapment and covalent linkage as protein-attachment mechanisms.

More particularly, an object of the invention is to provide such a method which takes advantage of a gel structure such as that described in above-referred-to U.S. patent application Ser. No. 483,055, to enhance the same significantly with respect to its desirable binding capabilities.

As is set forth in that patent application, the gel structure therein described, without any further treatment, is known to offer a protein-binding capability which represents a significant improvement over the then-existing prior art. Experiments with such a gel, during the past few months, have shown that further treatment of the gel, in accordance with the procedure proposed by the present invention, surprisingly and dramatically improves its already excellent performance. For example, in preparing test wells containing such a gel for conducting different assays, it was noticed that, in cases where the gel was (during pre-use rehydration) exposed (immersed) for significantly longer periods of time in water, it tended to exhibit an appreciable improvement in its protein-binding ability.

Exploring further this improvement in gel characteristics, it was discovered that immersing the gel for a relatively long time period, such as up to 2-hours, produced a very noticeable enhancement of binding capabilities. It was found further that, following such a treatment, the gel retained its enhanced condition even after it was allowed to dry for use at some later time.

An alternative to prior time-extensive water soaking involved subjecting the gel to plural, relatively vigorous, but not necessarily time-extensive, water-wash and dry cycles. This kind of treatment produced a similar enhancement.

Another type of comparably useful treatment procedure, discovered later, involved the immersion of a gel of the type described in water, followed immediately by one or more freeze/thaw cycles. Here, too, similar, appreciable enhancement occurred in the gel's protein-binding ability.

Study of pre- and post-treatment gels has given a relatively clear understanding of the mechanisms of improvement that take place during each of the specific procedures which have been tried and proven. Each procedure promotes the agglomeration of particles dispersed within the gel, which particles, during preliminary gel formation, are initially distributed relatively homogeneously (with uniform, non-agglomerated dispersion) throughout the body of the gel. Such particle agglomeration selectively enlarges the porosity of gel (below its exposed surface), and this appreciably improves the free flowability of liquids in the gel during an assay, with the result that a greater population of bindable protein gets exposed to available binding sites.

A further mechanism results from the fact that the particles in the gel are interconnected by elongated polymer filaments, or strands, which are the elements that "carry" the binding sites, with the latter being distributed along the lengths of the strands. Particle agglomeration stretches many of these strands, with the consequence that adjacent binding sites distributed along a strand are moved farther away from one another. This consequence greatly minimizes steric hindrance, and makes many more binding sites functionally available for the binding of proteins.

Expressing, therefore, the method of the invention in language that embraces the several known improvement techniques and mechanisms, the same includes:

1. Depositing on an immobilizing support structure a liquid mass of a gel-forming emulsion which, upon initial drying, is coalesceable into a thick gel-like like matrix film characterized by substantial, non-agglomerated matrix homogeneity;
2. After drying of such a mass, and following coalescence of the mass into a film of the type indicated, treating the resulting film to alter matrix homogeneity by producing agglomeration in the film; and
3. By such treating of the mass, establishing the object gel.

In one specific embodiment of the invention, the treating step is performed by subjecting the gel to multiple waterwash wash and dry cycles; in another specific approach, this step is performed by immersing the gel in water for a time-extended period; and in yet another procedure, the treatment step is performed by subjecting the gel to at least one freeze/thaw cycle.

The various objects and advantages attained by the invention will become more fully apparent as one reads the procedural descriptions which now follow.

DETAILED DESCRIPTION OF THE INVENTION

In all manners of practicing the invention, the procedure begins with the deposition on a suitable immobilizing support structure, such as within a test well of the type described in previously-referred-to patent application Ser. No. 399,855, of a liquid mass of a suitable gel-forming emulsion which, after it initially dries, coalesces into a thick gel-like matrix film. Preferably, this film is formed from a liquid prepared as a blend of several emulsion-type latex copolymer materials generally in accordance with the disclosure set forth in previously-referred-to patent application Ser. No. 483,055. The resulting film which forms upon drying of this liquid is substantially as described in that patent application, and in particular, takes the form of a matrix including particles dispersed substantially homogeneously throughout the matrix body, with polymer strands extending between and interconnecting these particles. The strands that interconnect the particles have potentially available protein binding sites distributed along their lengths.

Following such film formation, a treatment step is performed which alters the micro-structure of the matrix by promoting particle agglomeration and strand elongation, with resulting separation of binding sites which are disposed adjacent one another along the lengths of the strands. Three treatment steps are now known.

A preferred method of performing the treatment step is to immerse the immobilized gel in water, and to subject it to vigorous agitation therewithin for up to 30-minutes, followed by drying of the gel. This step, preferably, is repeated three to five times.

An alternative treatment step involves the immersion of the gel in water for a time-extended period, preferably about 2-hours, with subsequent drying of the gel.

A third alternative treatment step involves the quick immersion of the gel in water, followed by freezing at a temperature of about $-70°$ C, thereafter followed by thawing of the gel at room temperature and then allowing it to dry. Such a freeze/thaw cycle may be repeated several times.

Each of these procedures, employing different final treatment stages, yields a gel having a final structure which is the desired result from practice of this invention. More specifically, it produces a structure wherein particles in the gel have become agglomerated to enlarge the porosity of selected regions in the gel, and binding-site-containing strands have been elongated to separate and further space apart adjacent binding sites.

Micro-structure examination tests following each of these procedures has revealed a structure which can be described as follows.

The gel, on its immobilizing substrate (in this case a test well having a substantially flat bottom with slightly diverging walls) includes a surface membrane having a thickness of about 0.5-micron, with this membrane including pore openings of a slightly elliptical shape defined by maximum diameters ranging from about 0.1-micron to about 0.4-micron. The long axes of these pores are about twenty percent longer than the short axes.

The underlying bulk or body of the matrix consists of spherical globs, or particles, about 0.5-micron to about 1.0-micron in diameter, which particles are the inorganic elements suspended in the emulsion that forms the resulting film. These particles act as anchors for the ends of elongated polymer strands which extend between them, causing a thick webbing effect throughout the body of the gel. Typically, the majority of these polymer strands has lengths between about 2-microns to about 4-microns long (longer than the strands in the initially formed gel). The spaces between the strands and agglomerated particles represent void space, or pores, through which fluids and molecules can move relatively easily. Pore size increases from the top exposed surface of the film down toward the bottom, with the film having an overall thickness of about 50-microns. Pore space accounts for about seventy percent of the overall body of the film.

The micro-structure description just given represents quite accurately the central portion of the film.

Toward the perimeter of the film, adjacent the edges of the immobilizing well, structural conditions change. Here, the strands extend somewhat radially toward the outside of the film, with pores being much more linear than those described earlier, and with some strands reaching about 20-microns in length (a very significant elongation).

A gel so produced, and just described, which results from performance of the method steps of the invention, displays a protein-binding capability that represents a marked improvement over all known prior art binding substances. The object gel appears to combine the properties of both protein-entrapment, and protein-attachment by internal covalent linkage. For example, experience has shown that the gel produced in accordance with this invention is capable of binding ten to twenty times as much protein as a typical test tube plate, well or other prior-known immobilizing substrate, and about two to five times as much protein as can be bound in the untreated gel of the type described in application Ser. No. 483,055.

As a consequence of the extremely large protein-binding capability which results in a gel so produced, assays can be carried out rapidly on undiluted body samples containing high concentrations of a specific antigen or a specific antibody (the analyte sought).

With covalent-type binding occurring throughout the three-dimensional matrix which characterizes the object gel, very vigorous wash procedures can be applied without loss of protein. This situation speeds up the washing to as little 15-seconds, and hence further shortens the time required to perform an assay.

With particle agglomeration occurring during the procedure of the invention, porosity within the body of the gel increases, and this promotes and enhances the internal flow of liquids during an assay—thus increasing the population of protein which can be exposed to available binding sites. Further, as a consequence of the resulting strand elongation, adjacent binding sites along a strand become separated in a manner which greatly minimizes the problem of steric interference. Accordingly, there is a significant increase in the number of functionally available binding sites.

It should thus be apparent that the gel-forming method of the present invention produces a superior product for use in solid phase immunoassay testing.

While a preferred manner of practicing the invention, and alternatives thereto, have been described herein, it is appreciated that other variations and modifications may be made without departing from the spirit of the invention.

It is claimed and desired to secure by Letters Patent:

1. A method for preparing on an immobilizing support structure a three-dimensionally-extensive, water-swellable, particle-containing, protein-binding gel for the subsequent reception and binding therein of a selected bindable protein, said method comprising
    depositing on such a structure a liquid mass of a gel-forming emulsion which, upon initial drying, is coalesceable into a thick gel-like film adhered to the structure, with such film being characterized by substantial particle-dispersion homogeneity,
    after drying of such a mass, and following coalescence thereof into such a film, treating the resulting film to alter such particle homogeneity by agglomerating such particles in the film, and
    by said treating and agglomerating, establishing the object gel.

2. The method of claim 1, wherein said treating is performed by subjecting the film to a time-extensive water-immersion bath.

3. The method of claim 1, wherein said treating is performed by subjecting the film to multiple, time-successive, water-wash and dry cycles.

4. The method of claim 1, wherein said treating is performed by wetting the film, and by then subjecting it to at least one freeze/thaw cycle.

5. The method of claim 1, wherein said treating is performed by wetting the film, and by then subjecting it to plural freeze/thaw cycles.

6. A method for preparing on an immobilizing support structure a three-dimensionally-extensive, water-swellable, multiple-binding-site, non-sterically-hindered, protein-binding gel for the subsequent reception and binding therein of a selected bindable protein, said method comprising depositing on such a structure a liquid mass of a gel-forming emulsion which, upon initial drying, is coalesceable into a thick gel-like film adhered to the structure, with such film being characterized by substantial particle-dispersion homogeneity, with different particles interconnected by elongated material strands, each of which carries plural, longitudinally distributed protein binding sites, after initial drying of such mass, and following coalescence thereof into such a film, treating the resulting film to alter particle homogeneity by agglomerating particles in the film, and as a consequence of said agglomerating, stretching such strands to spread apart the binding sites distributed therealong.

7. The method of claim 6, wherein said treating is performed by subjecting the film to a time-extensive water-immersion bath.

8. The method of claim 6, wherein said treating is performed by subjecting the film to multiple, time-successive, water-wash and dry cycles.

9. The method of claim 6, wherein said treating is performed by wetting the film, and by then subjecting it to at least one freeze/thaw cycle.

10. The method of claim 6, wherein said treating is performed by wetting the film, and by then subjecting it to plural freeze/thaw cycles.

11. A method for preparing on an immobilizing support structure a three-dimensionally-extensive, water-swellable, multiple-binding-site, non-sterically-hindered, protein-binding gel for the subsequent reception and binding therein of a selected bindable protein, said method comprising depositing on such a structure a liquid mass of a gel-forming emulsion which, upon initial drying, is coalesceable into a thick gel-like film adhered to the structure, with different particles in such film interconnected by elongated material strands that carry plural longitudinally distributed protein binding sites, and after initial drying of such a mass, and following coalescence thereof into such a film, elongating such strands between such connected particles, thus to increase the separation between adjacent binding sites distributed therealong to minimize steric hindrance in the film and to maximize the film's protein-binding capability.

12. The method of claim 11, wherein said treating is performed by subjecting the film to a time-extensive water-immersion bath.

13. The method of claim 11, wherein said treating is performed by subjecting the film to multiple, time-successive, water-wash and dry cycles.

14. The method of claim 11, wherein said treating is performed by wetting the film, and by then subjecting it to at least one freeze/thaw cycle.

15. The method of claim 11, wherein said treating is performed by wetting the film, and by then subjecting it to plural freeze/thaw cycles.

* * * * *